(12) United States Patent
Gaiser et al.

(10) Patent No.: US 6,241,728 B1
(45) Date of Patent: Jun. 5, 2001

(54) LEFT ATRIUM ABLATION CATHETER AND METHOD

(75) Inventors: John W. Gaiser, Mountain View; Hong Li, Cupertino, both of CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/395,123

(22) Filed: Sep. 14, 1999

Related U.S. Application Data

(62) Division of application No. 08/993,211, filed on Dec. 18, 1997.

(51) Int. Cl.$^7$ .................................................. A61B 18/14
(52) U.S. Cl. .............................. 606/41; 607/99; 607/113; 607/122
(58) Field of Search .................................. 606/41, 47, 49; 607/99, 113, 122; 600/374, 381, 393

(56) References Cited

U.S. PATENT DOCUMENTS

| | | |
|---|---|---|
| 3,867,945 | 2/1975 | Long . |
| 4,117,836 | 10/1978 | Erikson . |
| 4,569,347 | 2/1986 | Frisbie . |
| 4,581,017 | 4/1986 | Sahota . |
| 4,838,879 | 6/1989 | Tanabe et al. . |
| 4,867,174 | 9/1989 | Skribiski . |
| 4,882,777 | 11/1989 | Narula . |
| 4,883,058 | 11/1989 | Ruiz . |
| 4,917,102 | 4/1990 | Miller et al. . |
| 4,920,980 | 5/1990 | Jackowski . |
| 5,147,315 | 9/1992 | Weber . |
| 5,171,232 | 12/1992 | Castillo et al. . |
| 5,246,007 | 9/1993 | Frisbie et al. . |
| 5,267,982 | 12/1993 | Sylvanowicz . |
| 5,295,493 | 3/1994 | Radisch, Jr. . |
| 5,304,131 | 4/1994 | Paskar . |
| 5,322,509 | 6/1994 | Rickerd . |
| 5,427,119 | 6/1995 | Swartz et al. . |
| 5,497,774 | 3/1996 | Swartz et al. . |
| 5,564,440 | 10/1996 | Swartz et al. . |
| 5,575,810 | * 11/1996 | Swanson et al. ........................ 607/99 |
| 5,673,695 | * 10/1997 | McGee et al. ........................... 606/41 |
| 5,785,706 | * 7/1998 | Bednarek ................................ 606/41 |
| 5,797,905 | * 8/1998 | Fleischman et al. ................... 606/41 |
| 5,814,028 | * 9/1998 | Swartz et al. .......................... 604/528 |
| 5,823,955 | * 10/1998 | Kuck et al. ............................ 600/374 |
| 5,842,984 | * 12/1998 | Avitall .................................. 600/374 |

FOREIGN PATENT DOCUMENTS

| | | |
|---|---|---|
| 0 670 168 A1 | 9/1995 | (EP) . |
| 0 711 573 A1 | 5/1996 | (EP) . |
| 0 727 236 A1 | 8/1996 | (EP) . |
| 0 727 239 A1 | 8/1996 | (EP) . |
| WO 95/10226 | 4/1995 | (WO) .............................. A61B/5/04 |
| WO 97/17904 | 5/1997 | (WO) .............................. A61B/17/36 |
| WO 99/30625 | 6/1999 | (WO) .............................. A61B/17/39 |

\* cited by examiner

Primary Examiner—Lee Cohen
(74) Attorney, Agent, or Firm—Daniel W. Latham; Beth L. McMahon; Harold R. Patton

(57) ABSTRACT

A left atrium ablation catheter (4), including a sheath (8) and a deflectable electrophysiology catheter (10) housed within the sheath, is used to ablate coronary tissue at a target site within the left atrium (LA) of a heart. The electrophysiology catheter has ablation electrodes (24) along the tip (10). The ablation catheter is introduced into the right atrium (RA) through either the superior vena cava (SVC) or the inferior vena cava (IVC). The distal open end of the sheath is guided through a punctured hole in the interatrial septum and into the left atrium. The distal end (20) of the sheath is either precurved or is steerable so the electrode tip can be directed to the coronary target site in the left atrium. The electrode tip is sized and configured to create the desired lesion at the target site without movement of the electrode tip.

34 Claims, 4 Drawing Sheets

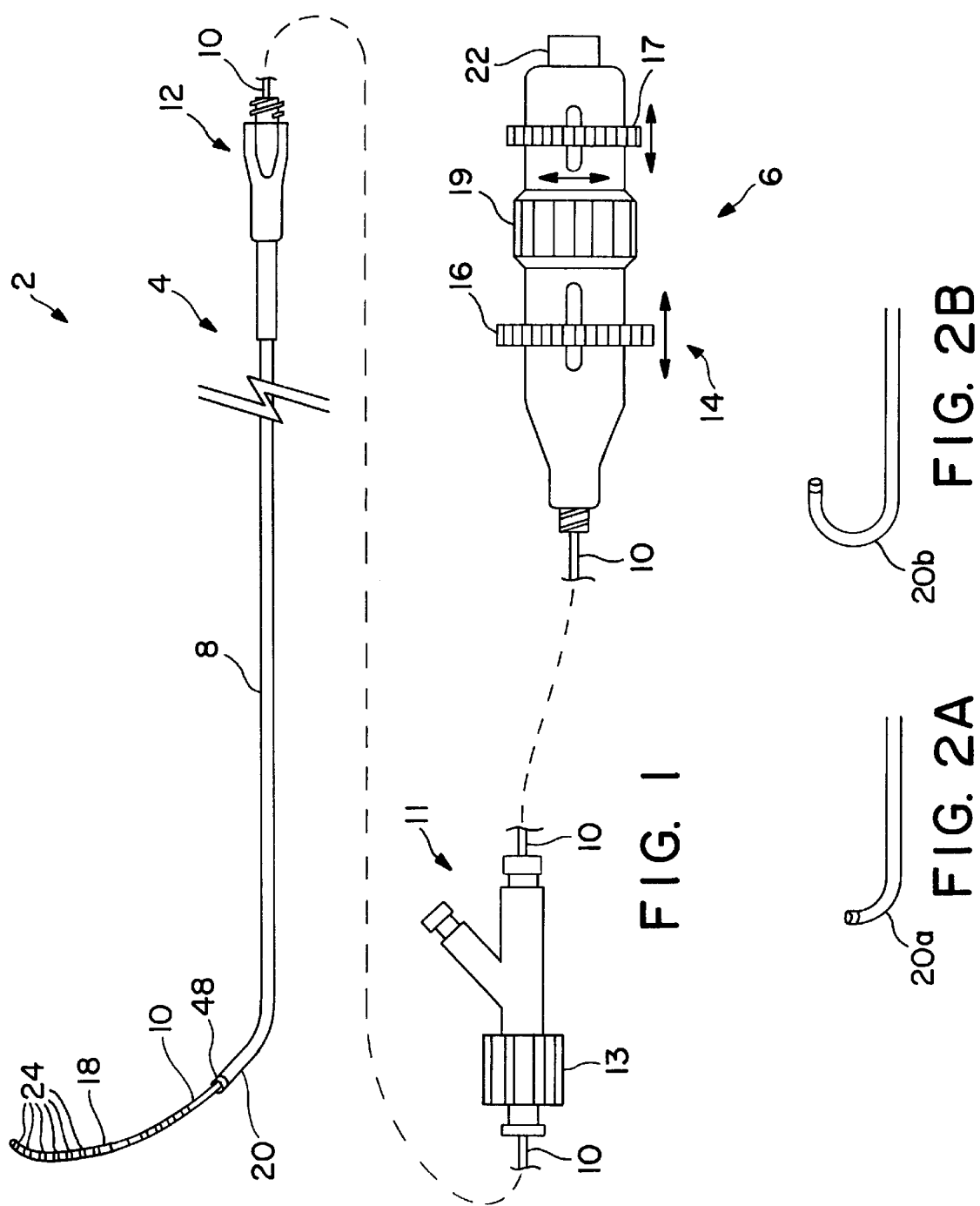

LEFT ATRIUM ABLATION CATHETER AND METHOD

This application is a division of application Ser. No. 08/993,211 filed Dec. 18, 1997.

BACKGROUND OF THE INVENTION

This invention relates to introducer sheaths used to introduce an electrophysiology catheter into the left atrium of the heart through a transseptal puncture and then direct the catheter to the target region within the left atrium.

The heart includes a number of pathways which are responsible for the propagation of signals necessary for normal electrical and mechanical function. The present invention is concerned with treatment of tachycardia, abnormally rapid rhythms of the heart caused by the presence of an arrhythmogenic site or accessory pathway which bypasses or short circuits the normal pathways in the heart. Tachycardias may be defined as ventricular tachycardias (VTs) and supraventricular tachycardias (SVTs). VTs originate in the left or right ventricle and are typically caused by arrhythmogenic sites associated with or without underlying heart disease. SVTs originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, drugs typically only mask the symptoms and do not cure the underlying cause. Implantable devices, on the other hand, usually can correct an arrhythmia only after it occurs. Surgical and catheter-based treatments, in contrast, will actually cure the problem usually by ablating the abnormal arrhythmogenic tissue or accessory pathway responsible for the tachycardia. The catheter-based treatments rely on the application of various destructive energy sources to the target tissue including direct current electrical energy, radiofrequency electrical energy, laser energy, and the like.

Of particular interest to the present invention, are radiofrequency (RF) ablation protocols which have proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable electrode is introduced to the appropriate heart chamber and manipulated so that the electrode lies proximate the target tissue. Radiofrequency energy is then applied through the electrode to the cardiac tissue to ablate a region of the tissue which forms part of the arrhythmogenic site or the accessory pathway. By successfully destroying that tissue, the abnormal signaling patterns responsible for the tachycardia cannot be sustained. Methods and systems for performing RF ablation by controlling temperature at the ablation site are described in U.S. Pat. No. 5,540,681 entitled "Method and System for Radiofrequency Ablation of Tissue."

Catheters designed for mapping and ablation frequently include a number of individual electrode bands mounted to the distal tip of the catheter so as to facilitate mapping of a wider area in less time, or to improve access to target sites for ablation. Such catheters are described in U.S. Pat. No. 5,445,148 entitled "Intracardiac Electrical Potential Reference Catheter." Mapping and ablation catheters may facilitate rotational positioning of the distal tip, either by rotating the entire catheter from the proximal end, or by exerting torque on a core wire secured to the distal tip without rotating the catheter body itself. See U.S. Pat. No. 5,545,200 entitled "Steerable Electrophysiology Catheter." Introducer catheters or sheaths having precurved distal ends have been used for guiding cardiac catheters as well as other types of catheters. See, for example, U.S. Pat. No. 5,147,315 and European Patent Application Publication No. 0670168.

Catheters used in radiofrequency ablation are inserted into a major vein or artery, usually in the neck or groin area, and guided into the chambers of the heart by appropriate manipulation through the vein or artery. Such catheters must facilitate manipulation of the distal tip so that the distal electrode can be positioned against the tissue region to be ablated. The catheter must have a great deal of flexibility to follow the pathway of the major blood vessels into the heart, and the catheter must permit user manipulation of the tip even when the catheter is in a curved and twisted configuration. Because of the high degree of precision required for proper positioning of the tip electrode, the catheter must allow manipulation with a high degree of sensitivity and controllability.

SUMMARY OF THE INVENTION

An ablation catheter, including a sheath and an electrophysiology catheter housed within the sheath, is used to ablate coronary tissue at a target site within the left atrium of a heart. The electrophysiology catheter has a tip with one or more ablation-capable electrodes along at least a portion of the length of the tip. The tip of electrophysiology catheter can be housed within the sheath while the sheath is being manipulated into position within the heart and then extended from the distal open end of the sheath.

The ablation catheter is introduced into the right atrium through either the superior vena or the inferior vena cava. The distal open end of the sheath is guided through a punctured hole in the interatrial septum and into the left atrium. The distal end of the sheath is either precurved or is steerable so that the distal end can be directed towards the desired region of the left atrium. The tip of the electrophysiology catheter is extended from the distal end of the sheath and is manipulated to contact the target site within the left atrium. Energy is then supplied to the tip of the electrophysiology catheter to ablate coronary tissue at a target site. The one or more electrodes are sized and positioned so that an elongate, therapeutically effective ablated lesion can be created at the target site without moving the tip along the target site.

It is generally preferred that the precurved portion of the sheath be at the distal end of the sheath. In some situations it may be desirable to provide an additional, proximal curve spaced apart from the distal end of the sheath to lie within the right atrium. Providing a proximal curve at this position helps to stabilize the sheath, which passed through the inferior vena cava or superior vena cava and into the right atrium, during the electrophysiology procedures. However, using such a dual-curve sheath limits the ability of the user to laterally deflect the curved distal end of the sheath by rotating the sheath about its longitudinal axis. In some situations this drawback is compensated for by the stability added through use of the proximal curve.

The curve at the distal end is preferably short or small. That is, the maximum lateral dimension of the curved distal end is preferably about 0.5 to 2.0 cm, more preferably about 1 cm. The radius of curvature of the curved distal end is preferably about 0.5 cm to 2 cm. By limiting the size of the curved distal end, the user can laterally deflect (torque) the curved distal end 360° so to direct the tip of the electrophysiology catheter passing through the open distal end of the sheath towards a great range of positions within the left atrium. This type of flexibility is not possible when the lateral dimension of the sheath in the left atrium is much larger, such as more than about 3 cm, as is found in some conventional catheters.

The catheter is typically introduced into the right atrium through the inferior/superior vena cava, and into the left atrium through a transseptal puncture at the fossa ovalis. This is typically accomplished with a needle and dilator passed through the sheath. After the distal end of the sheath is housed within the left atrium, the needle and dilator are removed from the sheath; this permits the distal end of the sheath, when precurved, to assume its normal curved shape. The somewhat elastic properties of the sheath help to maintain the sheath in position between the transseptal puncture and inferior/superior vena cava by the natural tendency of the sheath to straighten out after removal of the needle and dilator.

One of the advantages of a sheath with only the end being precurved is that the tip can be rotated (torqued) about its axis; a sheath with a proximal curved section within the right atrium cannot be so rotated. Another advantage is that the sheath can be slid through the septum to reposition the distal end of the sheath within the left atrium; this is not possible with many dual curve sheaths because the proximal curve becomes essentially enclosed within the right atrium between the inferior/superior vena cava and the transseptal puncture.

The sheath may be replaced by a dual sheath having an inner sheath, with a remotely steerable distal end, and an outer sheath. The outer sheath may have a precurved portion positionable within the right atrium for added stability.

An advantage of using a dual sheath with an outer sheath having a precurved portion at the inferior/superior vena cava is that additional stability is provided while maintaining the ability of the inner sheath to be rotated about its axis and extended longitudinally through the outer sheath. However, using a single sheath has the advantages of having a smaller diameter, less thickness, and the potential for creating less trauma, especially at the transseptal puncture, and less coagulation between the sheaths. With dual sheaths the inner sheath can be easily exchanged. This can be important when different positions within the left atrium are to be ablated, when mapping is to be undertaken and when the exact location of the target site is not known so that the type and shape of the curved distal end of the inner sheath may need to be changed during the procedure. An advantage of a sheath with a steerable or deflectable distal end is that the angle can be adjusted to accommodate different target sites within the left atrium; also, steerable sheaths are easier to insert and remove from the heart because they can have the curved distal end straightened while doing so.

Other features and advantages will appear from the following description in which the preferred embodiments have been set forth in detail in conjunction with the accompanied drawings.

BRIEF DESCRIPTION OF THE DRAWINGS

FIG. 1 is an overall view of a catheter assembly made according to the invention, the sheath having a precurved distal end, the curved distal end extending about 45° to the longitudinal axis of the sheath;

FIGS. 2A and 2B illustrate alternative embodiments of the precurved distal ends of the sheaths of FIG. 1 in which the precurved distal ends have curves of about 90° and 180°, respectively;

DESCRIPTION OF THE PREFERRED EMBODIMENTS

Figure 3:
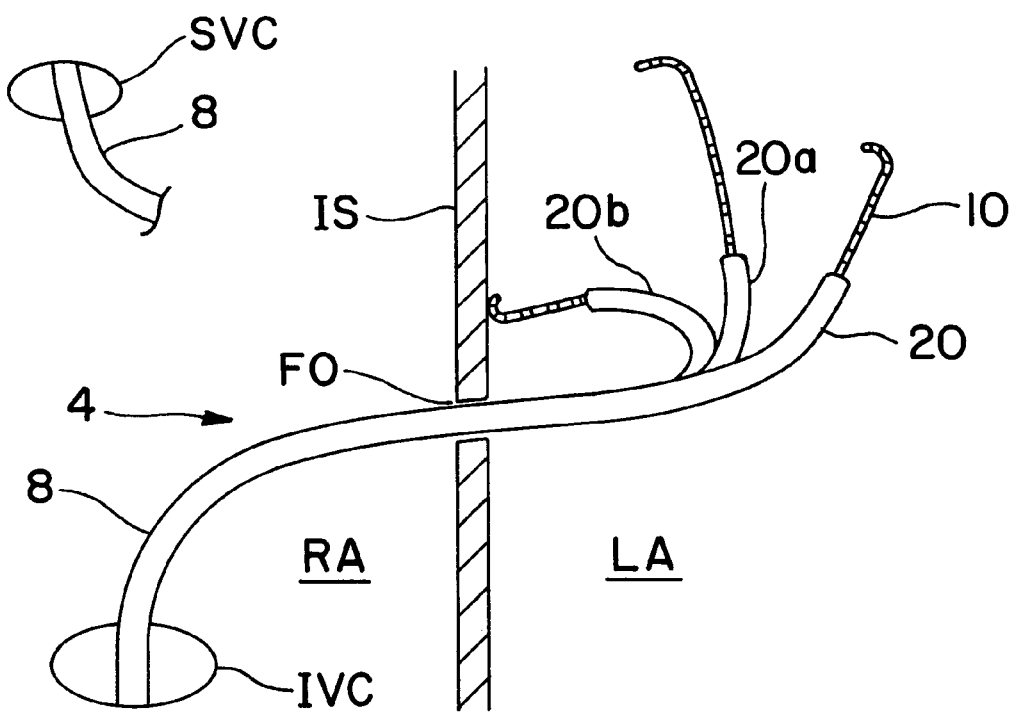
FIG. 3 illustrates, in simplified form, the distal portion of the ablation catheter of FIG. 1 within the heart, the ablation catheter illustrating the alternative curve angles for the distal ends of the catheters of FIGS. 2A and 2B as well as the curve angle of FIG. 1.

FIG. 1 illustrates a catheter assembly 2 including broadly a left atrium ablation catheter 4 extending from a proximal end adaptor 6. Catheter 4 includes a sheath 8 slidably housing an electrode catheter 10. Proximal end adaptor 6 includes a proximal adaptor 12, from which the proximal end of sheath 8 extends, a Y-adapter 11, including a hemostasis valve 13, and a handle 14, from which electrode catheter 10 extends. Adaptor 12, adaptor 11 and handle 14 are secured to one another using appropriate threaded fastener elements. Electrode catheter 10 can be slid longitudinally within hemostasis valve 13 and sheath 8 by the movement of handle 14. This assembly allows rotation of sheath 8 relative to catheter 10 and also injection of fluid between catheter 10 and sheath 8.

Longitudinal movement of manipulator 16 causes the distal portion of tip 18 of electrode catheter 10 to deflect radially, that is, into a curve. Handle 14 includes a second manipulator 17, which permits a proximal portion of tip 18 to be deflected radially, and a third manipulator 19 which permits tip 18 to be torqued so that the tip, when deflected radially, is deflected laterally (side-to-side) using the third manipulator. Handle 14 also includes an electrical connector 22 to provide electrical connections to the electrodes 24 carried by tip 18.

Electrodes 24 are preferably a series of separate band electrodes spaced along tip 18. Instead of or in addition to separate band electrodes, electrodes 18 could include one or more spiral electrodes. The electrodes could be electrically isolated from one another or some or all of the electrodes could be electrically connected to one other. In any event, the electrodes are shaped and positioned so that during ablation operations an elongate, continuous, therapeutically-effective ablated lesion is created at the target site within the left atrium of the heart without the need to move tip 18 along the target site. Preferably the length of each electrode 24 along tip 18 is about 4–12 mm, and more preferably about 7 mm. The spacing between each band electrode 24 is preferably about 0.5–3 mm, and more preferably about 1 mm. The total length of electrodes 24 is preferably at least about 1–2 cm long, and more preferably about 2–8 cm long.

Comparing FIG. 1 with FIGS. 2A and 2B, it is seen that distal end 20 can be made with a number of different precurved angles. In FIG. 1 the precurved angle is about 35–55°, typically about 45°. This angle tip is typically useful for directing tip 18 of electrode catheter 10 towards the left lateral atrium, such as the lateral wall or atrial appendage. See FIG. 3. The curved distal end 20a of the sheath shown in FIG. 2A is curved at about 75–105°, and more preferably about 90°, typically to contact a target site on the posterior wall of the left atrium, such as adjacent a pulmonary vein. FIG. 2B illustrates a distal end 20b which defines a curve of about 160° to about 195°, and more typically about 180°, typically to contact the wall of the interatrial septum. The radius of curvature of each distal end 20, 20a, and 20b is about 1 cm.

FIG. 3 illustrates, in simplified form, the passage of the distal portion of catheter 4 of FIG. 1 through the inferior vena cava IVC, into the right atrium RA, through a puncture in the interatrial septum IS at the fossa ovalis FO and into the left atrium LA. Also illustrated in FIG. 3 are the alternative embodiments of distal end 20 showing two additional curve angles. The introduction of the distal end of catheter 4 into right atrium RA is also suggested by the passage of sheath 8 into right atrium RA through superior ven cava SVC.

Figure 4:
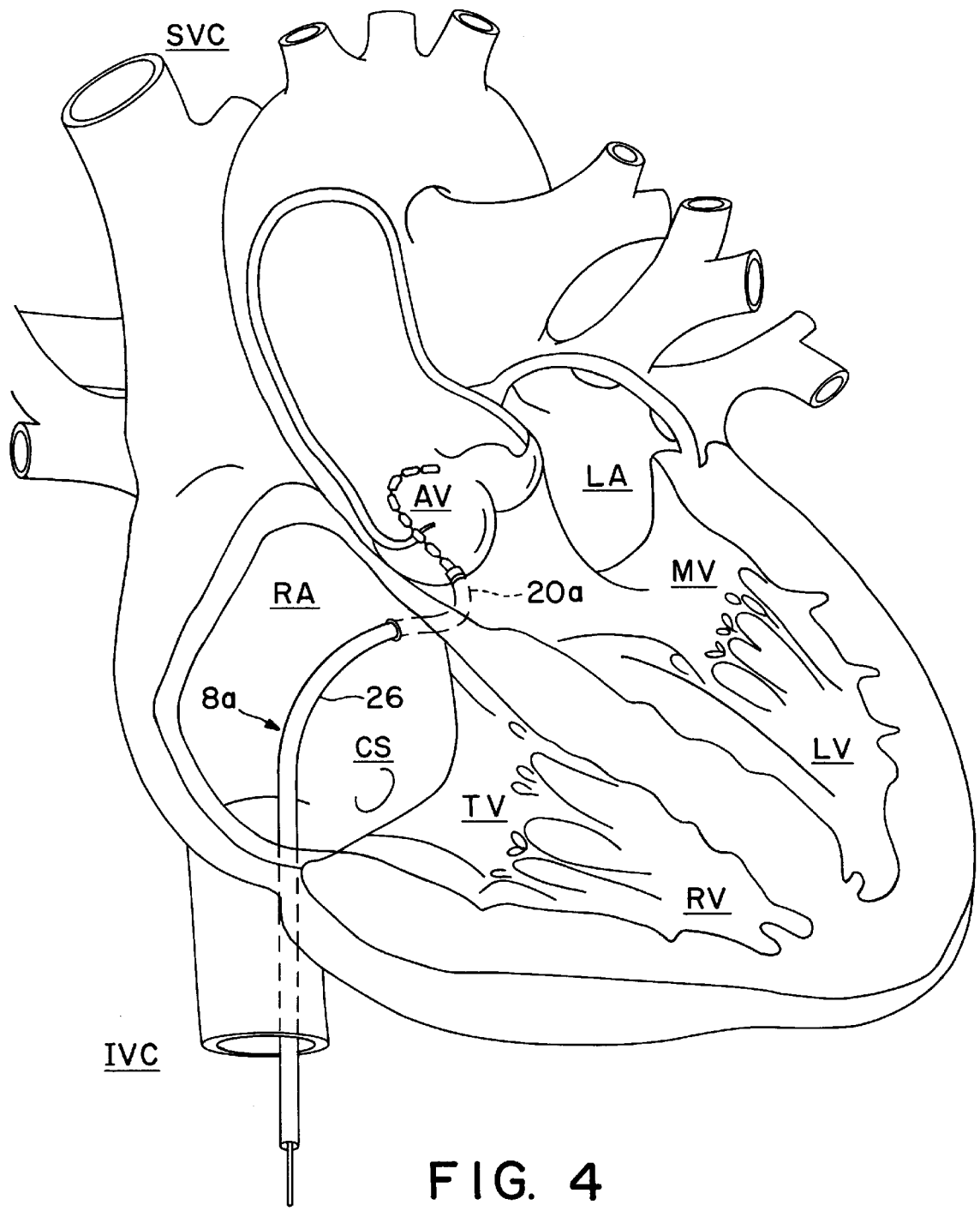
FIG. 4 illustrates the distal portion of an alternative embodiment of the catheter of FIG. 1 within a human heart in which the sheath has dual fixed curves and the curve at the distal end of the sheath is about a 90° curve as illustrated in FIG. 2A.

In the embodiments described above, sheath 8 has a single curve preformed in the sheath at distal end 20. In some cases it may be desired to use a sheath 8 having dual precurved portions. FIG. 4 illustrates a sheath 8a having a generally right-angle curve at distal end 20a, similar to the of FIG. 2A but also having a second, proximal curve 26 preformed into catheter 8a. Proximal curve 26 is situated within right atrium RA and is used to help stabilize ablatioi catheter 4 during use. FIG. 4 also illustrates several othe: features of the heart including the coronary sinus CS, a tricuspid valve TV, right and left ventricles RV and LV, mitral valve MV and atrioventricular valve AV.

Figure 5:
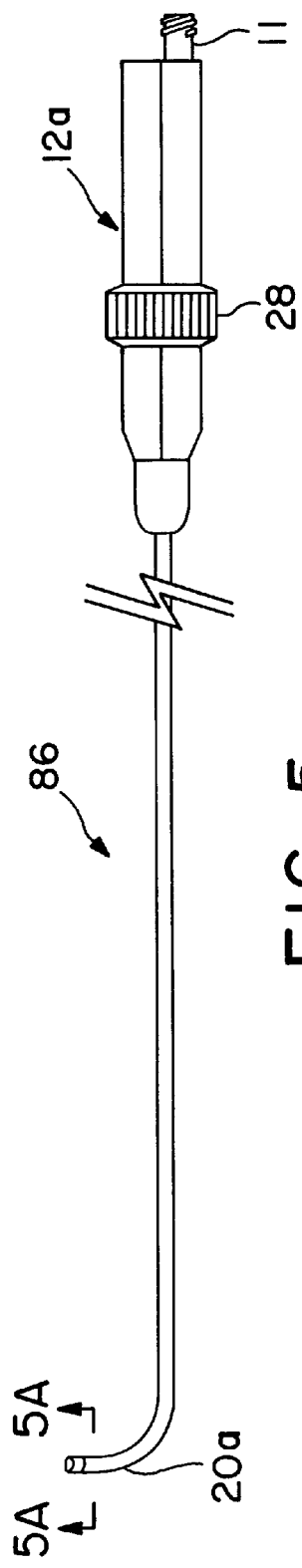
FIG. 5 illustrates an alternative embodiment of the sheath of FIG. 1 in which the sheath is a steerable sheath so that the distal end of the sheath can be radially deflected by moving a manipulator on the proximal end adapter.
Figure 5A:
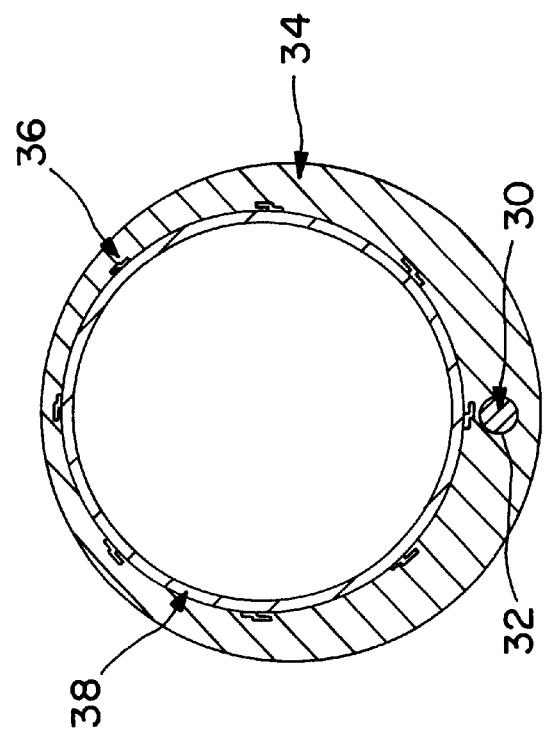
FIG. 5A is a cross-sectional view taken along line 5A—5A of FIG. 5.

FIGS. 5 and 5A illustrate a steerable sheath 8b which can be used in lieu of the fixed curved sheath of FIGS. 1, 2A. With sheath 8b a distal end 20c can be radially deflected from a straight configuration to the generally Ushaped configuration of FIG. 2B by pulling on a manipulator 28, which is part of a handle-type proximal adaptor 12a, in a proximal direction. Manipulator 28 is connected to the proximal end (not shown) of a manipulator wire 30, shown in FIG. 5A, which is housed within a secondary lumen 32 formed in the wall 34 of sheath 8b. Preferably, manipulator wire 30 has sufficient column strength so as to allow distal end 20c to be straightened by pushing on manipulator 28 in a distal direction which places wire 30 in compression. Wall 34 includes stainless steel flat braid wire 36 for structural support. Wall 34 is lined with a liner 38 which defines the main lumen 40 within sheath 8b. In the preferred embodiment, wall 34 of sheath 8b, as well as sheath 8a and 8, is made of PEBAX®, a polyamide polyether block copolymer from Elf Atochem, Inc. of Philadelphia, Pa. Liner 8 is preferably made of polyetherimide, sold under the trademark ULTEM® by GE PLASTICS, along most of the length of the sheath. However, liner 38 along distal end 20 is preferably made of PEBAX to provide the distal end with the desired flexibility.

Figure 6:
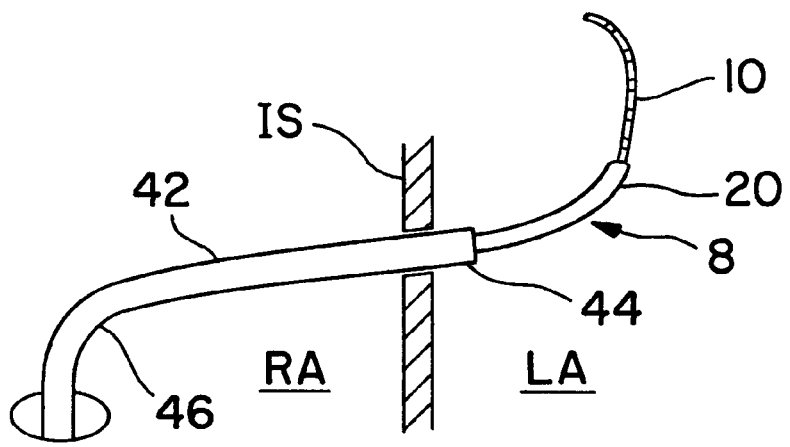
FIG. 6 is a simplified view similar to that of FIG. 3 illustrating the use of a dual sheath embodiment of the invention in which the outer sheath has a precurved portion, similar to the sheath of FIG. 4, near the inferior vena cava, the distal end of the outer sheath extending through the interatrial septum.

FIG. 6 illustrates the use of an outer sheath 42 having a distal end 44 which extends through interatrial septum IS into left atrium LA so to introduce sheath 8 into the left atrium. Distal end 20 sheath 8 may be precurved or it may be steerable, that is radially deflectable as in the embodiment of FIG. 5. Outer sheath 42 has a portion 46 within right atrium RA which assumes the shape of inner sheath 8 to provide stability for the catheter during use, as discussed with regard to the embodiment of FIG. 4. If desired, portior 46 could be replaced by a remotely deflectable portion 46.

In use, catheter 4 is transluminally positioned through a blood vessel for introduction of the distal end 20 through, for example, inferior vena cava IVC, into right atrium RA. The introduction can be accomplished with the aid of a conventional needle guidewire and dilator which both guides sheath 8 into position and also forms the hole at fossa ovalis FO, or elsewhere, in interatrial septum IS. Once sheath 8 is in the position shown in FIG. 3, the needle guidewire and dilator are removed and electrode catheter 10 is inserted through sheath 8 and out through distal end 20 of the sheath. Distal end 20 preferably has a radio-opaque marker 48 to permit the visualization of the position of distal end 20. The position of distal end 20 within left atrium LA can be changed by pushing or pulling a length of sheath 8 into or from the left atrium through the fossa ovalis. Also, the rotary orientation of distal end 20 can be changed by rotating proximal adaptor 12 about its longitudinal axis; doing so thus causes sheath 8 to torque along its length and causes the lateral deflection of curved distal end 20. Once properly oriented, tip 18 of electrode catheter 10 is extended through open distal end 20 until a desired length of electrode catheter 10 contacts the coronary tissue target site. Once properly in position, electrodes 24 can be energized, typically using RF energy, to create the desired elongate, continuous, therapeutically-effective ablation lesion at the target site without the need to move tip 18. After electrophysiology procedures are concluded, tip 18 of electrode catheter 10 can be withdrawn back into sheath 8 and sheath 8 can be withdrawn from the patient. With the embodiment of FIG. 4, the presence of proximal curve 26 prevents any substantial amount of torquing of sheath 8a thus minimizing any lateral deflection which might be able to be provided to distal end 20. However, as discussed above, the presence of proximal curve 26 does provide added stability, which may be desirable or needed in certain circumstances.

Any and all patents, patent applications and references referred to above are hereby incorporated by reference.

Modification and variation can be made to the disclosed embodiments without departing from the subject of the invention as defined in the following claims.

What is claimed is:

1. A method for ablating coronary tissue within the left atrium of a heart comprising the following steps:

selecting an ablation catheter assembly having a proximal end, the ablation catheter assembly comprising a sheath having a precurved distal open end and a precurved section spaced apart from the precurved distal open end, and a deflectable electrophysiology catheter housed within the sheath and extendable from the distal open end, said electrophysiology catheter comprising an ablation-capable tip;

introducing the distal open end of the sheath into the right atrium through a chosen one of the superior vena cava and the inferior vena cava;

positioning the precurved section within the right atrium near said chosen one of the superior vena cava and the inferior vena cava;

guiding the distal open end from the right atrium, through the interatrial septum and into the left atrium;

manipulating the sheath so the precurved distal open end has a desired orientation;

extending the tip from the distal open end and directing the tip so the tip contacts a target site; and ablating coronary tissue at said target site.

2. The method according to claim 1 further comprising the step of axially deflecting the tip of the electrophysiology catheter.

3. The method according to claim 1 wherein the selecting step comprises the step of choosing an electrophysiology catheter having a plurality of electrodes.

4. The method according to claim 3 wherein said choosing step is carried out so said electrodes create a continuous linear lesion during said ablating step without the need to move the tip from the target site.

5. The method according to claim 1 wherein the sheath selecting step is carried out so that the precurved, distal open end has a lateral dimension of about 0.5 to 2 cm.

6. The method according to claim 1 wherein the sheath selecting step is carried out so the precurved distal open end has a curve of about 35° to 55°.

7. The method according to claim 6 wherein the extending and directing step includes the step of laterally deflecting the ablation-capable tip by rotating the proximal end of the catheter assembly.

8. The method according to claim 7 wherein the extending and directing step is carried out so the tip contacts at least one said target site at the roof, the floor and the mitral annulus in the left atrium.

9. The method according to claim 6 wherein the tip extending and directing step is carried out so the tip contacts a target site at the lateral left atrium.

10. The method according to claim 9 wherein the tip contacts the target site of the lateral wall.

11. The method according to claim 9 wherein the tip contacts the target site of the atrial appendage.

12. The method according to claim 1 wherein the sheath selecting step is carried out so the precurved distal open end has a curve of about 75° to 105°.

13. The method according to claim 12 wherein the extending and directing step includes the step of laterally deflecting the ablation-capable tip by rotating the proximal end of the catheter.

14. The method according to claim 13 wherein the extending and directing step is carried out so the tip contacts at least one said target site at the roof, the floor and the mitral annulus in the left atrium.

15. The method according to claim 12 wherein the tip extending and directing step is carried out so the tip contacts a target site on the posterior wall of the left atrium.

16. The method according to claim 15 wherein the tip contacts the target site at or adjacent to a pulmonary vein of the posterior left atrium.

17. The method according to claim 1 wherein the sheath selecting step is carried out so the precurved distal open end has a curve of about 160° to 195°.

18. The method according to claim 17 wherein the extending and directing step includes the step of laterally deflecting the ablation-capable tip by rotating the proximal end of the catheter.

19. The method according to claims 18 wherein the extending and directing step is carried out so the tip contacts at least one said target site at the roof, the floor and the mitral annulus in the left atrium.

20. The method according to claim 17 wherein the tip extending and directing step is carried out so the tip contacts a target site on the septal wall of the left atrium.

21. The method according to claim 20 wherein the tip contacts the target site at the fossa ovalis.

22. The method according to claim 1 wherein the ablation catheter selecting step comprises the step of selecting a dual sheath having the sheath as an inner sheath surrounded by a second outer sheath, said inner and outer sheaths including inner and outer distal open ends.

23. The method according to claim 22 wherein said dual sheath selecting step comprises the step of selecting an inner sheath having a remotely steerable inner distal open end.

24. The method according to claim 23 wherein the dual sheath selecting step comprises the step of selecting an outer sheath having a precurved portion and further comprising the step of positioning the precurved portion of the outer sheath within the right atrium near the chosen one of the superior vena cava and inferior vena cava.

25. The method according to claim 23 wherein the dual sheath selecting step comprises the step of selecting an outer sheath with said outer distal open end being not precurved.

26. The method according to claim 25 further comprising the step of torquing said inner sheath following the guiding step.

27. The method according to claim 22 wherein the dual sheath selecting step comprises the step of selecting an outer sheath with said outer distal open end being not precurved.

28. The method according to claim 22 further comprising the step of torquing said inner sheath following the guiding step.

29. The method according to claim 1 wherein the selecting step comprises the step of selecting an electrophysiology catheter having electrodes along about 1–2 cm of said tip.

30. The method according to claim 1 wherein the selecting step comprises the step of selecting an electrophysiology catheter having electrodes along about 2–8 cm of said tip.

31. The method according to claim 30 wherein the ablating step comprises the step of creating a linear lesion about 2–8 cm long without moving the tip from the target site.

32. The method according to claim 1 wherein the ablating step comprises the step of creating a linear lesion without moving the tip from the target site.

33. The method according to claim 1 wherein the manipulating step is carried out by pulling and/or pushing on a manipulator wire housed within a second of first and second lumens formed in the sheath.

34. A method for ablating coronary tissue within the left atrium of a heart comprising the following steps:

selecting an ablation catheter assembly having a proximal end, the ablation catheter assembly comprising a dual sheath having an inner sheath surrounded by an outer sheath, said inner sheath having a remotely steerable inner distal open end and said outer sheath having a precurved portion, said ablation catheter assembly further having a deflectable electrophysiology catheter housed within the dual sheath and extendable from a distal end of said dual sheath, said electrophysiology catheter comprising an ablation-capable tip;

introducing said distal end of said dual sheath into the right atrium through a chosen one of the superior vena cava and the inferior vena cava;

positioning the precurved portion of the outer sheath within the right atrium near the chosen one of the superior vena cava and the inferior vena cava;

guiding said distal end of said dual sheath from the right atrium, through the interatrial septum and into the left atrium;

manipulating said dual sheath so the inner distal open end of the inner sheath has a desired orientation;

extending the tip from the inner distal open end and directing the tip so the tip contacts a target site; and ablating coronary tissue at said target site.

* * * * *